(12) United States Patent
Klemp et al.

(10) Patent No.: US 7,247,152 B2
(45) Date of Patent: Jul. 24, 2007

(54) DISPOSABLE ABSORBENT ARTICLE WITH CONTAINMENT STRUCTURE

(75) Inventors: Walter V. Klemp, Houston, TX (US); Paul M. Ducker, Vancouver, WA (US); Daniel D. Gardner, Jr., Petosky, MI (US); Scott W. Sneed, Friendswood, TX (US)

(73) Assignee: Associated Hygienic Products LLC, Duluth, GA (US)

( * ) Notice: Subject to any disclaimer, the term of this patent is extended or adjusted under 35 U.S.C. 154(b) by 93 days.

(21) Appl. No.: 09/418,902

(22) Filed: Oct. 15, 1999

(65) Prior Publication Data

US 2002/0151860 A1 Oct. 17, 2002

(51) Int. Cl.
*A61F 13/20* (2006.01)
*A61F 13/15* (2006.01)

(52) U.S. Cl. .......................... 604/385.01; 604/385.24; 604/385.101

(58) Field of Classification Search ............... 604/358, 604/385.01, 385.101–385.24, 385.3
See application file for complete search history.

(56) References Cited

U.S. PATENT DOCUMENTS

| | | | |
|---|---|---|---|
| 4,662,877 A | 5/1987 | Williams | 604/385 A |
| 4,738,677 A | 4/1988 | Foreman | 604/385 R |
| 4,753,646 A | 6/1988 | Enloe | 604/385 R |
| 4,816,025 A | 3/1989 | Foreman | 604/385 R |
| 4,938,754 A | 7/1990 | Mesek | 604/385.2 |
| 4,998,929 A | 3/1991 | Björksund et al. | 604/385.2 |
| 5,019,066 A | 5/1991 | Freeland et al. | 604/385.2 |
| 5,026,364 A | 6/1991 | Robertson | 604/385.1 |
| 5,304,159 A | 4/1994 | Tanji et al. | 604/385.2 |
| 5,397,318 A | 3/1995 | Dreier | 604/385.2 |
| 5,415,649 A | 5/1995 | Watanabe et al. | 604/385.2 |
| 5,439,459 A | 8/1995 | Tanji et al. | 604/385.2 |
| 5,449,353 A | 9/1995 | Watanabe et al. | 604/385.2 |
| 5,558,660 A | 9/1996 | Dreier | |
| 5,569,227 A | 10/1996 | Vandemoortele et al. | 604/382 |
| 5,672,166 A | 9/1997 | Vandemoortele | 604/385.2 |
| 5,817,087 A | 10/1998 | Takabayashi et al. | 604/385.2 |

(Continued)

FOREIGN PATENT DOCUMENTS

| | | |
|---|---|---|
| EP | 0570980 | 5/1993 |
| JP | 24364 | 12/1987 |

*Primary Examiner*—Michele Kidwell
(74) *Attorney, Agent, or Firm*—Morris & Amatong, P.C.; Alberto Q. Amatong, Jr.

(57) ABSTRACT

A disposable absorbent article is disclosed that is partially defined by a pair of longitudinally extending side edges and a pair of end edges extending between the side edges, and includes a topsheet layer, a backsheet layer, and an absorbent core disposed between the topsheet and the backsheet. The disposable absorbent article also has a pair of side wall structures each having a pair of oppositely positioned end portions. A first side wall structure extends generally longitudinally between the core and one of the side edges and the other side wall structure extends generally longitudinal between the core and the other side edge. Further, an end strip constructed from an elastic material is positioned substantially adjacent each one of the end edges, and extends laterally between the side edges. Each of the end strips includes a fixed elastic end section disposed adjacent the end edge and secured to the topsheet, a fixed intermediate section positioned longitudinally inward of the fixed end section, and a movable, elastic inward section positioned longitudinally inward of the intermediate section.

17 Claims, 5 Drawing Sheets

U.S. PATENT DOCUMENTS

| | | | |
|---|---|---|---|
| 5,827,259 A | 10/1998 | Laux et al. | 604/385.2 |
| 5,931,826 A | 8/1999 | Faulks et al. | 604/385.2 |
| 5,938,652 A | 8/1999 | Sauer | |
| 5,941,864 A | 8/1999 | Roe | 604/378 |
| 6,010,490 A | 1/2000 | Freeland et al. | 604/385.1 |
| 6,017,336 A | 1/2000 | Sauer | 604/385.1 |
| 6,039,906 A * | 3/2000 | Sageser et al. | 264/156 |
| 6,056,732 A | 5/2000 | Fujioka et al. | 604/385.1 |
| 6,135,988 A * | 10/2000 | Turner et al. | 604/387 |
| 6,258,076 B1 * | 7/2001 | Glaug et al. | 604/387 |

\* cited by examiner

DISPOSABLE ABSORBENT ARTICLE WITH CONTAINMENT STRUCTURE

BACKGROUND OF THE INVENTION

The present invention relates generally to disposable absorbent articles such as a diaper, a training pant, or an incontinence pant.

Disposable absorbent articles are increasingly popular products. Use of disposable diapers and training pants now exceeds, by far, the use of cloth diapers. Further, advancements made in the design of disposable feminine hygiene product have produced products which offer improved comfort and utility and, thus, the use of these products have also increased. Advancements have also been made in the design of disposable adult incontinence products which are designed to control and absorb involuntarily bowel and bladder discharge associated with many medical conditions.

Disposable diapers are designed with structural features intended to enhance fit, comfort, and/or minimize leakage. In this regard, various structural designs have been developed and incorporated into diapers. For example, disposable diapers may have standing inner leg cuffs which are combined with elastic leg gatherers, such as the structures disclosed in U.S. Pat. No. 4,704,116 to Enloe, and in U.S. Pat. No. 4,695,278 to Lawson. In these structural designs, the leg cuffs and elastic leg gatherers are designed to work together so as to retain waste within a central core portion of the diaper. In another variation, a pair of "T"-shaped cuffs are disposed longitudinally on either side of the central core (see e.g., U.K. Patent Application No. 2,216,393).

These prior art designs have been effective to varying degrees in containing discharge from a wearer's body. The complexity in these structural designs also vary and may require multiple fabrication steps. For example, cuff/elastic gatherer combinations require the creation of both a cuff and an elastic gatherer which must be separately applied and which must be engineered to work together. "T"-shaped cuffs generally require additional engineering and manufacturing expense to place a "T"-shaped elasticized gasket upon a distal edge of a cuff. In an alternate design that is disclosed in U.S. Pat. No. 5,643,243 to Klemp, a diaper is provided with elasticized unitary cuffs. Each unitary cuff includes multiple strands of elastic material and provides the sole elasticizing means for containing waste within the crotch region of the diaper.

Many of these diapers and other garments are also designed with an hourglass contoured shape which improves the fit and comfort of the diaper. A disadvantage of such contoured garments is that their design generally requires the use of complex high precision machinery to form necessary intricate shapes, thereby significantly increasing the production cost associated with the garment. Moreover, many of these garments are formed from rectangular absorbent articles, typically cut in assembly line fashion from moving webs. To form a garment from such a rectangular piece of absorbent material, material is typically cut away from the longitudinal edges of the absorbent article and discarded during formation of the leg holes. While such contoured garments generally provide a more comfortable fit, these garments may be prone to leakage along the edges of the contoured region.

SUMMARY OF THE INVENTION

It is one of several features and objects of the present invention to provide an improved disposable absorbent article.

It is another feature and object of the invention to provide at least one such disposable absorbent article characterized by improved containment capabilities and/or features adapted to minimize leakage.

It is yet another feature and an object of the present invention to provide at least one such disposable article having a containment pocket for the purpose of retaining body exudates.

It is yet another feature and an object of the present invention to provide at least one such disposable absorbent article having a structure applicable to the waist regions of the article so as to provide a waistband portion and/or a portion of a containment wall of a containment pocket.

Therefore, in accordance with one aspect of the present invention, there is provided a disposable absorbent article (e.g., a diaper, a training pant, etc.) having a pair of longitudinally extending side edges and a pair of end edges extending laterally between the side edges. The inventive article includes a topsheet layer, a backsheet layer, and an absorbent core disposed between the topsheet and the backsheet. The article further includes a pair of side walls, each of which has a pair of oppositely positioned end portions and an intermediate portion disposed therebetween. A first side wall is positioned generally between the core and one of the side edges and extends generally in the longitudinal direction. A second side wall is positioned generally between the core and the other side edge, and extends also in the longitudinal direction.

The inventive article also includes a pair of end strips (e.g., patch, material covering or similar structure), each of which is fixed generally intermediate the core and one of the end edges, and extends between the side edges (e.g., laterally along at least a portion of the lateral distance between the side edges). Each of the end strips includes an elastic inward section that is spaced away from the topsheet and the absorbent core and has a pair of side portions. Each of these side portions is secured to an end portion of one of the side walls, such that the side walls are biased generally upwardly. The end strip may also function to apply tension across the waist regions of the article and/or apply a contractile force between the side walls. Such an end strip may also be referred to as a tension strip or tensioner.

In accordance with another aspect of the invention, a disposable absorbent article is provided having a containment pocket with a depth dimension. The pocket is disposed generally in the crotch region of the article and is bounded by a substantially continuous containment wall that extends generally upwardly to retain exudates therein. The containment wall has at least two elastic wall sections made preferably from an elastic material and preferably distinct from the topsheet. The containment wall also includes at least two intermediate wall sections each of which is disposed between one elastic wall section and another elastic wall section. Each of the elastic wall sections has a central portion and oppositely disposed side portions and each of the intermediate wall sections has oppositely disposed end portions. Each of the side portions of the elastic wall sections is secured to an end portion of one of the intermediate wall sections such that the intermediate wall section is biased generally upwardly. In one embodiment, the article includes an end strip generally secured to each one of the waist regions. Each end strip includes an elastic inward section that is spaced away from the topsheet and the absorbent core to form one of the elastic wall sections of the containment wall.

In accordance with yet another aspect of the present invention, a disposable absorbent article is provided having at least one end strip that is fixed intermediate the core and one of the end edges and extends between the side edges (up to or short of the end edges). It should be noted that the end strip may be relatively wide or narrow and may have a greater or lesser longitudinal dimension than a lateral dimension. The inventive end strip may include a first section that is preferably elastic and preferably disposed adjacent the end edge (e.g., fixed along the end edge) and a second section disposed longitudinally inward of the first section (e.g., fixed to the topsheet). Together, the first section and the second section may be formed from the same materia (e.g., an elastic material). Also, these two sections may be referred to as the waist section of the end strip. In one embodiment, the first section is formed from an elastic material and is secured adjacent the end edge to form a waistband portion of the article. The second section is characterized in that the first section is substantially more elastic than this second section. Preferably, the second section is formed from the same elastic material as the first section and/or the rest of the end strip, but is substantially de-elasticized by providing a plurality of voids, apertures, or slits therein.

The end strip of the inventive article also includes a third section positioned longitudinally inward of the second section. This third section has an inward portion that is spaced away from the topsheet and the absorbent core (e.g., moveable). The third section is preferably made from an elastic material and may be secured to longitudinally extending side walls of the article (as described above) so as to apply a contractile force between the side walls and/or bias the side walls generally upwardly. In this way, the elastic inward sections and the generally upwardly biased side walls may form the substantially continuous peripheral wall of a containment pocket disposed in the crotch region of the article. In one embodiment, this third section is referred to as a soffit section.

The depth dimension of the pocket may be defined as the vertical distance between an inward edge of the inward portion and the average elevation of the top surface of the core. This depth dimension is preferably greater than about ¼" and, more preferably, between about ½" and about 4". Most preferably, the depth dimension of the pocket is between about ¾" and about 2".

Moreover, the side walls may be constructed such that an intermediate portion of the side edges generally parallel with (and spaced laterally from) the core may be secured with the inward sections and is biased generally upwardly. In one embodiment, the side wall includes such an intermediate portion of the side edges, a portion of the topsheet and/or an elastic member(s) (e.g., an elastic strand) secured to the side edges and/or the topsheet.

Other and further objects, features, and advantages of the present invention will be apparent from the description provided herein of presently preferred embodiments of the invention, given for the purpose of disclosure, and taken in conjunction with the accompanying drawings.

DETAILED DESCRIPTION OF THE DRAWINGS

FIGS. 1–4 depict a disposable absorbent garment or article 10 embodying the invention. The disposable absorbent article 10 is of the type which can be placed against or in proximity to the body of a wearer so as to absorb and to contain various bodily exudates. In particular, the disposable absorbent article 10 depicted in the figures and, described in more particular detail below, is in the form of a diaper 10. It should be noted, however, that the present invention is applicable to a variety of disposable absorbent articles and garments, including training pants and a variety of adult incontinence products. Accordingly, the present invention is not intended to be limited to the structures and the processes specifically described and illustrated herein. For purposes of description, the following discussion will be directed to an exemplary disposable diaper only.

In addition, the invention will be described in the context of its various configurations and aspects. It should be appreciated that alternative arrangements of the invention may comprise various combinations, which include one or more of the various configurations and aspects of the invention.

Figure 1:
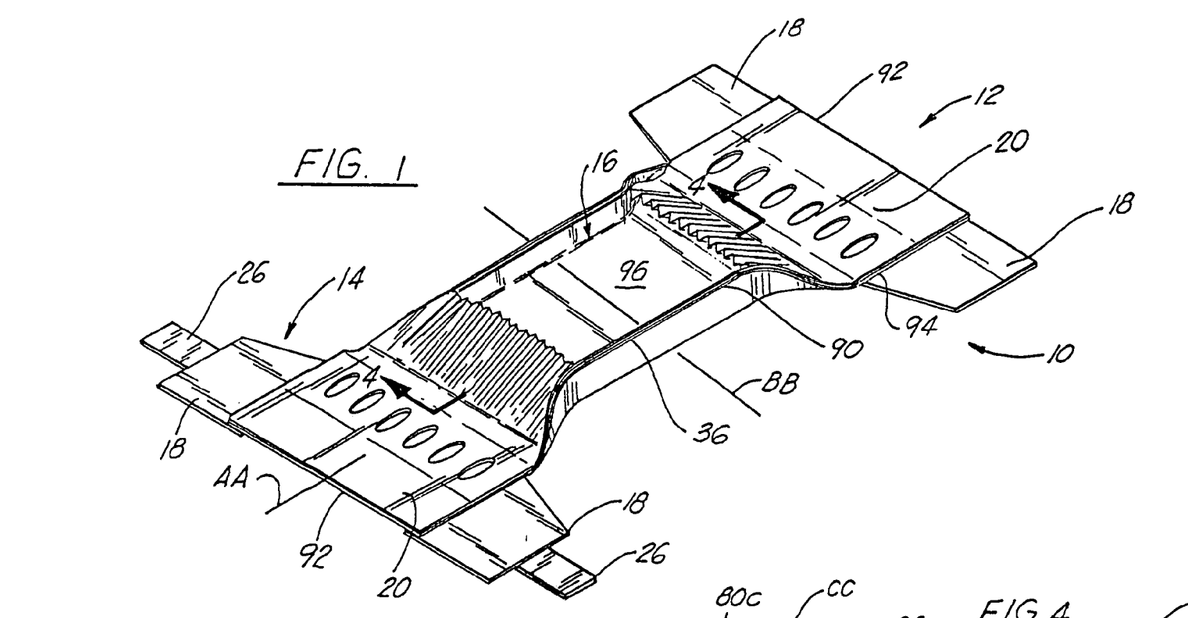
FIG. 1 is a perspective view of a disposable absorbent article according to the present invention.

FIG. 1 illustrates, in perspective view, a composite web structure of the diaper 10 in a generally flat and unfolded configuration which it assumes during one point in the manufacturing process (when it is stretched in the longitudinal direction). As will be explained further below, the web structure may be subsequently trimmed, folded, sealed, welded and/or otherwise manipulated to form a disposable diaper 10 in a finished or final form.

To facilitate description of the diaper 10 embodying the invention, description will refer to a longitudinally extended axis AA, a laterally extending central axis BB, a pair of longitudinally extending side edges 90, and a pair of end edges 92 which extend between side edges 90. Along the longitudinal axis AA, the diaper 10 includes a first end region or front waist region 12, a second end region or back waist region 14, and a crotch region 16 disposed therebetween. Each of the front and back waist regions 12, 14 is characterized by a pair of ear regions or ears 18, which are located on either side of a central body portion 20 and extend laterally from the side edges 90. A fastening structure 26 (e.g., a conventional tape fastener) is affixed to each of the ears 18 along the back waist region 14 of the diaper 10.

As shown in the Figures, the diaper 10 is characterized by a generally hourglass shape wherein an intermediate portion of the side edges 90 (which is generally in the area of the crotch region 16) is biased generally upwardly (i.e., to partially form upwardly disposed longitudinal walls). When the diaper 10 is worn about the waist of the wearer, the front waist region 12 is fitted adjacent the front waist area of the wearer, the back waist region 14 is fitted adjacent the back waist area, and the crotch region 16 fits about and underneath the crotch area. To properly secure the diaper 10 to the wearer, the ears 18 of the back waist region 14 are brought around the waist of the wearer and toward the front and into alignment with the ears 18 of the front waist region 12. This securing surface may be located on or provided by the interior or exterior surface of the front waist region 12. Alternatively, the fasteners 26 may be located on the ears 18 of the front waist region 12 and made securable to the ears 18 of the back waist region 14. In one further example, a tab structure having hook structures may be attached to the ears 18 of the waist region 14 and made securable to loop members found on the front waist region 12. Such a "hook and loop" concept (and other generally known fastening structures) is generally known and practiced in the art and may be incorporated into the present invention design by one skilled in the art having access to the disclosure provided herein.

Figure 2:
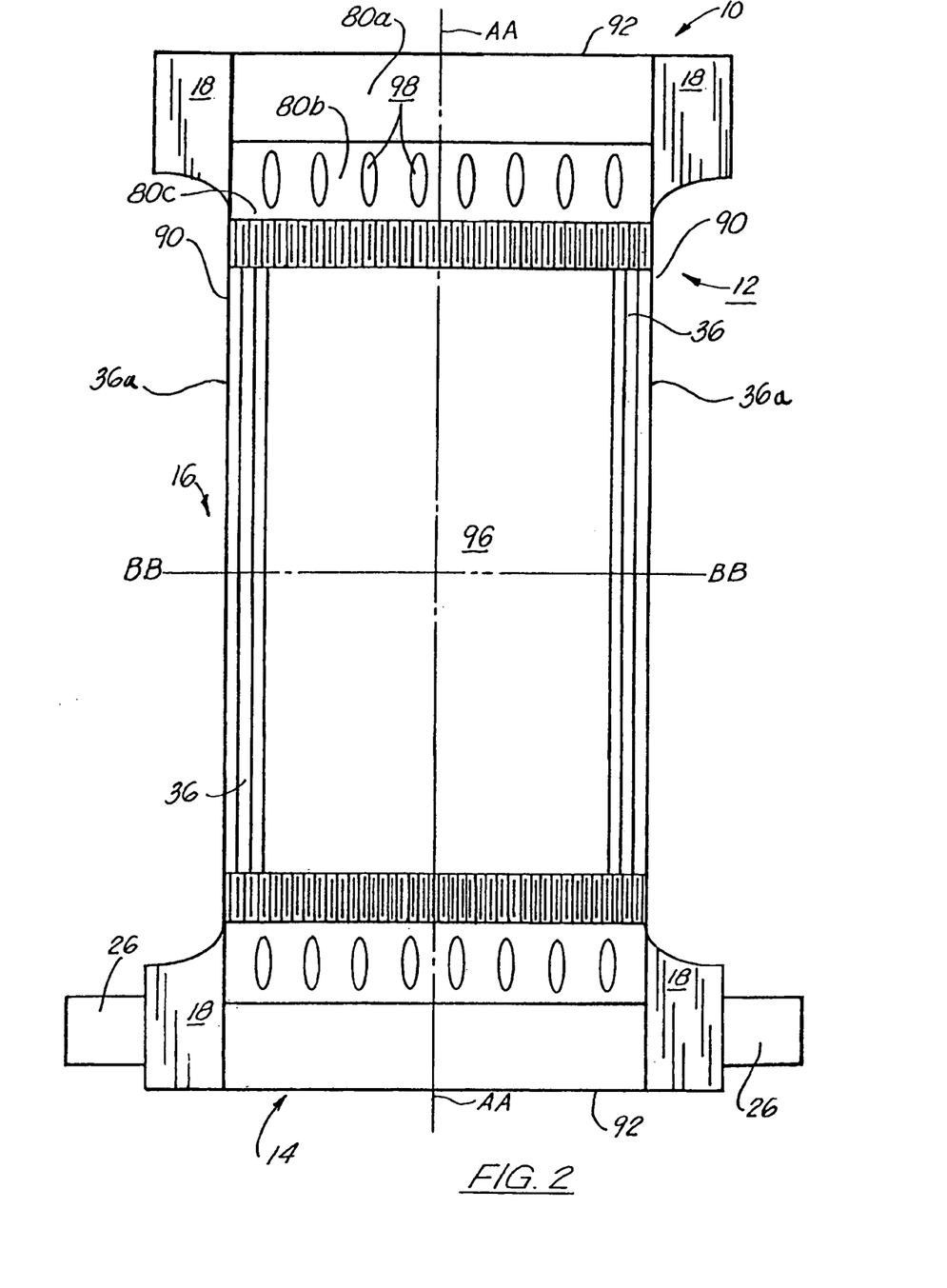
FIG. 2 is a top view of the disposable absorbent article in FIG. 1 in a flat, extended condition.
Figure 3:
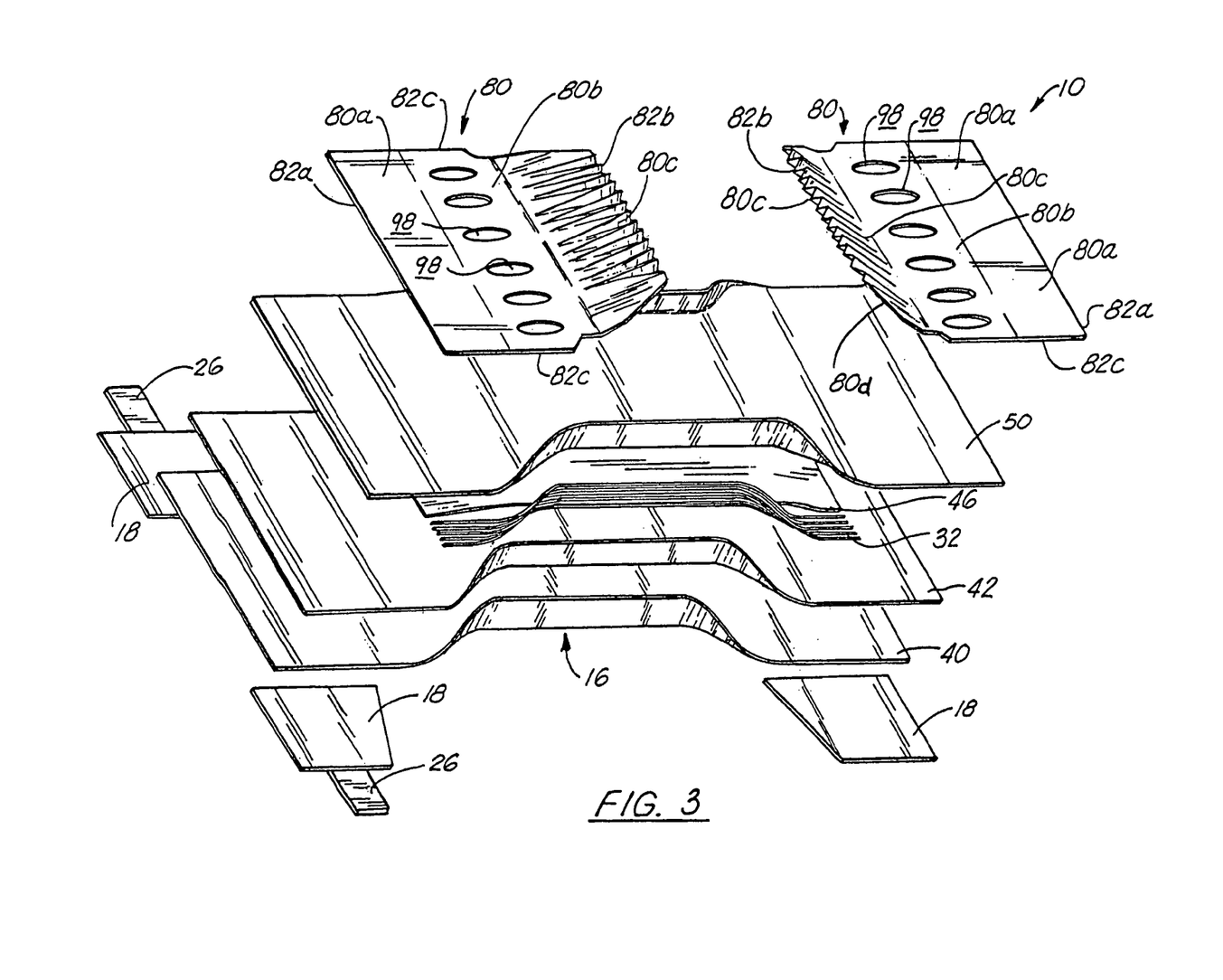
FIG. 3 is an exploded view of the disposable article of FIG. 1.

The diaper 10 of the present invention also features one or more longitudinally stretchable elastic members or leg elastics 32 positioned adjacent each of the two side edges 90 of the diaper 10 (see FIG. 3). When the diaper 10 is properly worn by the wearer, each leg elastic 32 encircles a leg of the wearer and provides a quasi-seal thereabout which substantially prevents leakage from the interior of the diaper 10. Such leg elastics 32 may be applied in the stretched or extended condition. In one application of invention, the elastics 32 are placed between the topsheet 50 and the backsheet 40 in the stretched condition, and, then, attached to one or both of the sheets 50, 40 (i.e., by glue or other adhesive). When subsequently released, the elastics 32 retract and form barrier cuffs, gathered leg regions or leg gatherers 36 as it pulls adjacent material therewith (see also FIGS. 1 and 2).

Figure 4:
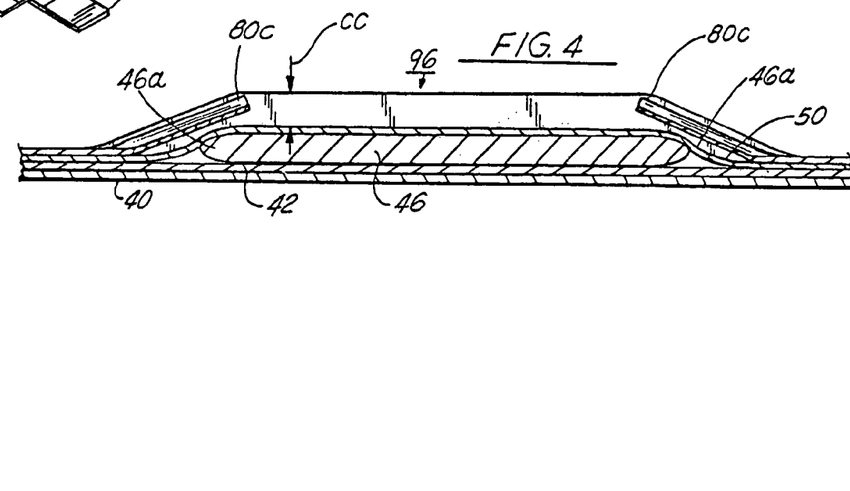
FIG. 4 is a cross-sectional view of the disposable article taken along line 4—4 of FIG. 2.

Now referring primarily to the exploded view of FIG. 3, a diaper 10 according to the invention typically features two to five layers. These five layers include a non-woven backsheet 40, a film barrier 42, a core 46, a topsheet 50, and a pair of end strips or tensioner members 80 disposed above the topsheet 50. FIG. 4 provides a cross-sectional view that depicts all five layers and their respective structural relationships. In an alternative embodiment, the diaper 10 may include an acquisition layer disposed between the core 46 and the topsheet 50 (such a construction is described in more detail below). In yet another embodiment, the inventive diaper may utilize a multipurpose material as one of the layers (which provides multiple functions). In this way, the number of layers that is required may be reduced, and, in some embodiments, a thinner diaper structure results.

The tensioner member or tensioner 80 is preferably a single piece elastic strip having an outside end edge 82*a*, an inside end edge 82*b*, and a pair of opposite side edges 82*c*. As shown in FIGS. 2 and 4, the tensioner 80 is disposed over the surface of the topsheet 50 such that the outside end edge 82*a* is secured adjacent (e.g., aligned with) the end edge 92 of the diaper 10 (i.e., at each of the front waist region 12 and the back waist region 14). In the embodiment of FIGS. 1–4, the tensioner 80 generally extends transversely between the ears 18, i.e., from adjacent one side edge 90 of the diaper 10 to adjacent the opposite side edge 90. Along the longitudinal direction, the tensioner 80 extends inwardly from adjacent end edge 92 toward the crotch region 16 and just over the area of the core 46 (at an angle direction spaced from the core 46 and topsheet 50). Thus, the tensioner 80 occupies a substantial portion of the front waist region 12 or back waist region 14 except in the ear regions 18.

The tensioner 80 may be formed from elastic film, foam, a combination of non-woven material and a stretchable film that is laminated together or a combination of two or more of these materials or laminate. The tensioner 80 may also be formed from a non-woven material with elastic strands or elastic nonwoven material. In one suitable construction, the tensioner is formed primarily from an open cell polyurethane foam available from General Foam of Paramus, N.J. In yet another suitable construction, the tensioner is formed from an elastic apertured film available from Tredegar Industries of Cincinnati, Ohio.

The tensioner 80 is preferably comprised of at least three distinct sections: a fixed elasticized section 80*a* (not shown in FIGS.) preferably secured adjacent one of the end edges 92 of the diaper 10, a fixed de-elasticized section 80*b* which extends inwardly (in the direction of the crotch area 16) from the elasticized section 80*a*, and an elasticized soffit section 80*c* which extends inwardly (in the direction of the crotch area 16) from the de-elasticized section 80*b*. In the flat, extended condition of the diaper, as shown in FIG. 1, there is a vertical separation or vertical distance CC between the inside edge 80*d* of the soffit section 80*c* and the top surface of the core 46. Both the fixed elasticized section 80*a* and the fixed de-elasticized section 80*b* are secured (using any one of a number of securing means known in the art, e.g., by melting, sonic molding, or by applying adhesives) to a top surface of the top sheet 50.

Preferably, the tensioner 80 is secured to the top surface of the top sheet 50 while it (the tensioner 80) is disposed in the stretched condition and such that, when the secured tensioner 80 is subsequently released, the fixed elastic section 80*a* contracts with the adjacent portion of the front or back waist region 12, 14 intact. This forms a structure that provides the same functional advantages as a traditional waistband along the end edges 92 of the diaper 10. Accordingly, when the two end edges 92 are joined around the waist of the wearer, the two fixed elastic sections 80*a* are also joined and function generally as waistbands to secure the diaper 10 snugly around the waist of the wearer. Moreover, the two fixed elastic sections 80*a* form a quasi seal around the waist of the wearer to prevent waste captured by the diaper 10 from leaking past the top or end edges 92.

The de-elasticized section 80*b* is formed with a plurality of voids or apertures 98 each of which functions to de-elasticize the immediate area adjacent the apertures 98. Collectively, the plurality of apertures 98 function to substantially de-elasticize the elastic material of the de- elasticized section 80*b*. The apertures 98 are typically created by slitting or cutting that section of the tensioner 80 at a stage in the manufacturing process before application of the tensioner 80 to the top sheet 50 or other subsurface layer. The size and number of apertures 80 are determined so as to prevent unnecessary weakening of the tensioner 80 and to guard against propagation of tears in the de-elasticized section 80*b*. Alternatively, de-elasticization is achieved by a heat deformation process which de-elasticizes the elastic material by applying heat on the targeted material before application of the tension 80 to the topsheet 50 or other subsurface layer. In other embodiments, de-elasticization is achieved by the addition of stiffening materials at the targeted area. In further embodiments, other methods of de-elasticization known to those skilled in the art are utilized. One advantage provided by the existence of a de-elasticized or non-elastic section is that the end strip can have elastic properties but the tendency of waist regions to contract (i.e., in the longitudinal direction) or crumple up is minimized.

It should be noted that the de-elasticized section 80*b* and the fixed section 80*a* are referred to herein as two sections of the tensioner 80 (e.g., a waist section of the tensioner 80) only for descriptive purposes. However, in the embodiment depicted in FIGS. 1–4, the fixed elastic section 80a and the fixed de-elasticized section 80b are formed from the same elastic material and differ only in that the de-elasticized section 80b has been applied and configured with the apertures 98. In alternative embodiments, these two sections may, indeed, differ substantially structurally and/or from a manufacturing standpoint.

Absent of voids or apertures, the soffit section 80c of the diaper 10 depicted in the drawings retains the strength and elasticity of the elastic material from which the tensioner 80 is formed. The soffit section 80c may also be referred to as the inward section of the tensioner 80. In FIGS. 1–4, the sofftit section 80c is also formed from the same elastic material from which the fixed elastic section 80a and the fixed de-elasticized section 80b are formed. The soffit section 80c extends inwardly from the de-elasticized section 80b and upwardly (i.e., at an angle) away from the topsheet 50. As best shown in the cross sectional view of FIG. 4, the soffit section 80c extends inwardly to the extent that it is over a longitudinal edge portion 46a of the core 46.

In one aspect of the invention, substantially all of the central portion of the soffit section 80c is free from and is spaced from the top sheet 50, while the side portions or lateral edges of the soffit section 80c are secured to the top sheet 50 and the distal edges 36a of the leg gathers 36. As a result, the tensioner 80 functions to pull at least the intermediate portions of the side edges 90 or, more appropriately, the regions of the side edges (including the leg gathers 36) upwardly (by applying a contractile force across the waist region 16). These side edge regions are biased or brought to and maintained in an upstanding position along the crotch region 16 (see, e.g., FIGS. 1 and 3), to form upright side wall structures or side walls. As will be further explained below, these upstanding wide walls perform a containment or sealing function, as well as enhance the fit and comfort of the diaper 10.

As best shown in FIG. 1, the diaper 10 takes on an hourglass shape that is particularly advantageous to the fit and sealing ability of the diaper 10. This fit is further enhanced by the upstanding disposition of the leg gathers 36 (provide side walls) and the tension provided in the front and back waist regions 12, 14 by the tensioner 80. Another advantage provided by the inventive diaper design is that the hourglass shape of the diaper may be attained without having to cut leg openings into the composite web structure during the manufacturing process.

In yet another aspect of the invention, the combination of the upstanding side walls (including the barrier cuffs or leg gathers 36) and the elasticized soffit section 80c on both the front waist region 12 and the back waist region 14 of the diaper creates a retention compartment or containment pocket 96 at the crotch section region 16. This retention compartment 96 is generally deeper than conventional containment or central core areas. The retention compartment 96 may be characterized as having a depth dimension generally equal to the vertical distance CC or the vertical distance between the inward edge 80d and the average elevation of the top surface of the core 46. This depth dimension CC is generally greater than about ¼" and up to about 4", but preferably will be between ¾" and 2" (as measured when the diaper 10 is in the flat, extended condition). The upstanding leg gathers 36 serve as one set of retaining sidewalls for the retention compartment 96 while the oppositely-facing elasticized soffit sections 80c serve as retaining end walls of the retention compartment 96. The elasticized soffit sections 80c are, in one regard, particularly adapted to provide such a function because it extends upwardly and well above the core 46. Thus, the retention compartment 96 may be referred to as having at least two elastic wall sections and at least two intermediate wall sections each disposed between elastic wall sections. In alternative embodiments, the wall sections may be disposed in other areas of the article 10. The relatively deep retention compartment 96 of the present invention provides an improved structure and means for receiving and retaining body exudates in the central portion of the diaper 10. It should be noted, however, that the design of a deep retention compartment 96 is also applicable and advantageous in other disposable articles or garments 10.

In alternative embodiments of the present invention, the end strip may consist of more or less than three distinct sections. Further, the sections of the end strip may not be necessarily formed from the same material. Further yet, the end strip may be formed integrally as one piece with the topsheet or may include a portion of the topsheet. Additionally, the end strip may not necessarily be disposed adjacent the end edges and, in partially forming a containment wall of a retention compartment, may not necessarily be disposed in the front or back waist regions of the article. Some of these variations are discussed below. However, it should be noted that these variations or adaptations will be apparent to one skilled in the art upon reading the description and viewing the drawings provided herein.

In one alternative embodiment of the present invention, the tensioner consists of only the soffit section. Such a soffit section may be formed from an elastic material or a composition including an elastic material (e.g., elastic film or elastic strand(s)). The soffit section may be wholly elastic or include a portion having elastic properties. For example, the soffit may include a central portion that is formed from an elastic material (or otherwise elasticated), and side portions which are secured to the ends of barrier cuffs, leg gathers or portions of the side edges (so as to create upstanding side edge regions or side walls). Further, the soffit section may be formed by creating a fold with a portion of the topsheet and by elasticating at least a portion of the fold.

In yet another alternative embodiment, the disposable absorbent article according to the invention may include a traditional waistband structurally separate from the end strip and/or soffit section. Such a diaper may also include a non-elastic or de-elasticized section between the waistband and the soffit section. Further, such a non-elastic or de-elasticized section may be integrally formed with the soffit section.

In yet another embodiment, an end strip according to the invention is disposed one each lateral side of the core. Such an end strip includes an elastic or tensioned portion and may be formed, at least partially, with the topsheet and/or barrier cuffs or leg gathers. The end strip includes side portions which are secured to a side wall structure which may be formed from a folded portion of the topsheet, so as to bias the folded portion upwardly. Accordingly, a containment pocket of the disposable absorbent article is formed having a generally upwardly disposed and substantially continuous peripheral wall that is provided by the end strips and the side walls.

It should be further noted that, by locating an end strip at certain localized regions of the article as in the various embodiments described above, a tensioned or contracting zone is created in those regions. The tensioned zones provide one or more functions including providing a portion of a containment wall of a containment pocket. The tensioned zones may also function to bias generally upwardly a structure disposed adjacent each end of the tensioned zone such that the structures form side walls of the containment wall. In some embodiments, the tensioned zones also form a waistband portion.

Figure 5:
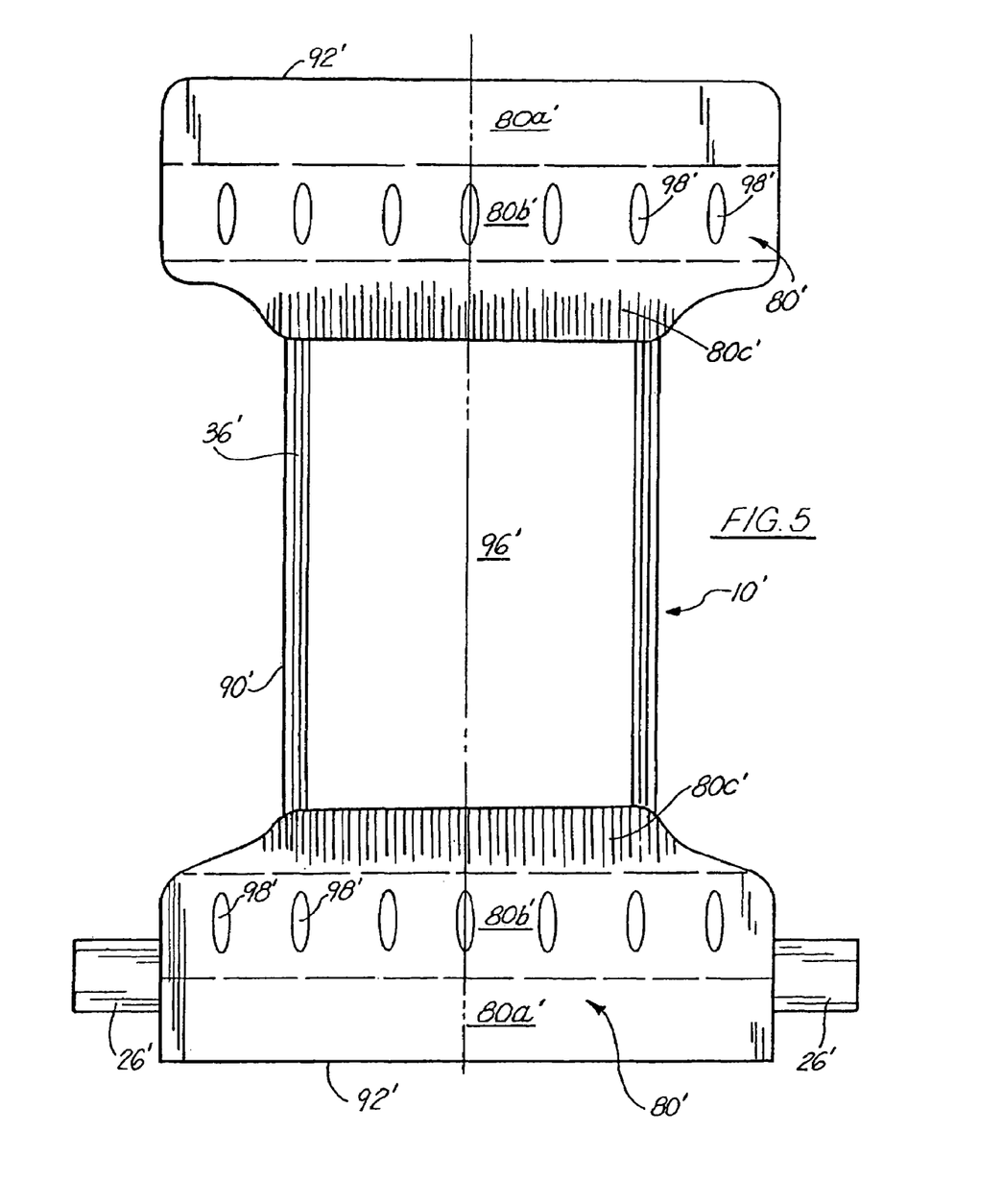
FIG. 5 is a top view of a disposable absorbent article in a flat, extended condition according to an alternative embodiment of the present invention.
Figure 6:
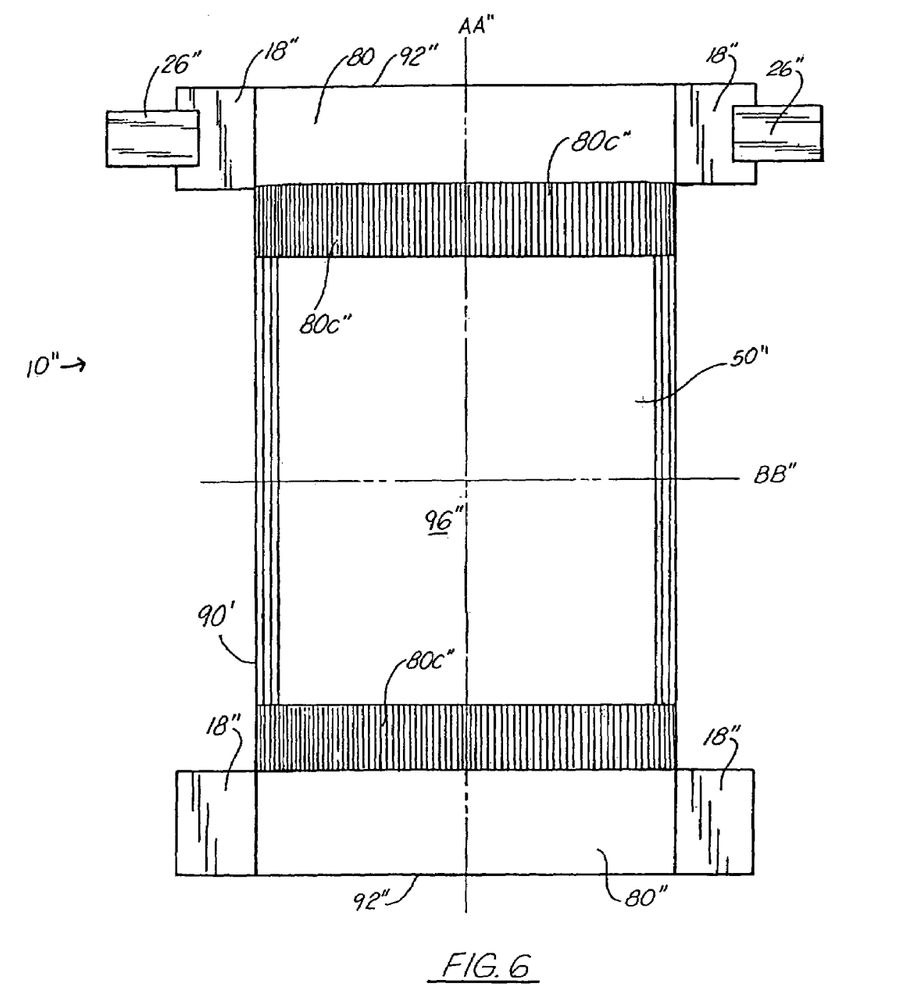
FIG. 6 is a top view of a disposable absorbent article in a flat, extended condition according to yet another embodiment of the present invention.

FIGS. 5 and 6 each depict a plan view of an alternative embodiment of the invention having a tensioner 80', 80" that forms one portion of the containment wall of a retention compartment or containment pocket 96', 96". In the embodiment depicted in FIG. 5, the diaper 10' employs a tensioner 80' having a fixed elasticized section 80a', a fixed de-elasticized section 80b', and a movable soffit section 80c'. One feature of this diaper 10" is a tensioner 80' that extends laterally over the ear regions. This side portion may be die-cut to form, along with the topsheet and/or the backsheet, a stretchable ear region or side panel 18" of the diaper 10'. The diaper 10" of FIG. 6 employs another end strip or tensioner 80" consisting of a soffit section 80c". The soffit section is fixed on one edge to the topsheet 50" and extends immediately inwardly therefrom and away from the topsheet 50".

The following discussion expands upon the description of certain components described above which may be incorporated into a disposable absorbent article according to the invention:

Backsheet and Film Layer

A backsheet employed by a disposable absorbent article according to the invention may be constructed from a number of different suitable materials and, preferably, will have a breathable or vapor permeable attribute (distinguishing it from a liquid permeable material) such that air can pass therethrough. For example, the backsheet may be formed from a combination of a liquid permeable, nonwoven material and a film barrier that is laminated onto the nonwoven material. This type of backsheet design is in contrast to the design employed by the embodiment of FIGS. 1–4, wherein the backsheet 40 and the film barrier 42 are separate and distinct from one another. In either design, the film barrier may or may not be vapor permeable.

One construction suitable for incorporation with the design of the present invention, and more particularly, for the backsheet includes an outer layer of spunbond polypropylene fiber with a basis weight of about 14–25 grams per square meter (available from BBA nonwovens, of Simpsonville, S.C.) and a polyethylene film of about 0.5 mil. (0.0005 inches) thickness adhesively laminated to the outer layer. Such a polyethylene film is available from, and manufactured by Tredegar Industries of Cincinnati, Ohio. This film may be laminated using adhesive available from National Starch and Chemical Company of Bridgewater, N.J. Yet another suitable construction for the backsheet includes a web of spunbond or SMS (spunbond/meltblown/spunbond) nonwoven material and a breathable or nonbreathable film(s) of 0.5 mil. to 2.0 mil. thickness.

The backsheet covers at least the core 46, but preferably extends laterally beyond the core toward the side edges and the end edges of the article. The nonwoven portion of the backsheet may be provided only where the leg gathers turn upward, such that the section of the backsheet covering the core area is film.

Topsheet

The topsheet 50 in FIGS. 1–4 may be constructed from any one of a wide range of liquid and vapor permeable hydrophilic materials. The topsheet may consist of or include non-woven webs of natural fibers (e.g., wood or cotton) or synthetic fibers (e.g., polypropylene or polyester), a combination of such webs or fibers, or apertured film. One suitable topsheet material is a 15 gsm spunbond polypropylene from Avgol Non-wovens of Holon, Israel. In addition, the topsheet may be treated with a surfactant to facilitate liquid transfer, especially at a central zone or area of the topsheet located over the core and an inner surface of the topsheet may be treated with a chemical to increase the surface tension of liquids which pass through it.

In the embodiment of FIGS. 1–4, the topsheet 50 is formed from a single piece or sheet of material that covers substantially the entire area of the disposable absorbing article 10, including substantially all of the front waist region 12, back waist region 14, and crotch region 16. Further, ear region 18 of disposable absorbent article 10 is formed from the same single topsheet material and, thus, may be referred to as being unitary with and forming lateral extensions of the topsheet material.

Alternatively, the topsheet may be formed from multiple different materials, which vary across the width of the topsheet. Such a multiple piece design allows for the creation of preferred properties in different zones of the topsheet. For example, the topsheet may comprise a center section above the absorbent core that is made of a hydrophilic material and a pair of leg cuff sections that are formed substantially from a hydrophobic material.

Absorbent Core

The absorbent core 46 of FIGS. 1–4 is generally centered about the longitudinal axis AA and lateral axis BB of the diaper 10, and is firmly secured between the topsheet 50 and the backsheet 40. The core 46 is preferably made from any one of several compositions (known in the art) which are adapted to absorb bodily liquids received through the topsheet 50. For example, the absorbent core may include a fluffed wood pulp component which provides wicking capability and structural integrity, and a high absorbency material (e.g., super absorbent) for containing liquids. The core may also include additional additives to provide other specific properties such as baking soda to provide improved odor absorbency. It should be noted, however, that the disposable absorbent article 10, according to the invention, is adapted to utilize absorbing cores of varying shapes and compositions.

Many absorbent cores known in the art are comprised of two components: a high absorbency material (or super absorbent material) and an absorbent composite. As expected, the majority of the volume of such an article (i.e., bulkiness) is due to the composite. The high absorbency material may be one of numerous compounds. A suitable material may include inorganic materials such as polyvinyl alcohol, polyacrylates, various grafted starches, and cross linked polysodiumacrylate. Further, the high absorbency material may be manufactured and utilized in the diaper in numerous forms including, but not limited to, particles, fibers, foams, and layers. On the other hand, the absorbent composite is generally a composite material such as a defiberized fiber, or a wood pulp.

Another relatively new material for core composition is the "MicroThin Absorbent Composite" under the "Mega-Thin" brand name. This material has been developed by Japan Absorbent Technology Institute of Japan. The material is a composite of SAP (superabsorbent polymer), MFC (microfibrillated cellulose) and non-woven which is characterized by its lighteners, thinners and softeners. See PCT Application PCT/JP97/04606, which is hereby incorporated by reference).

An application of any such material to the present structure according to the invention will be apparent to a person skilled in the art. In addition, the specific structural configuration of the disposable absorbent article of the invention may also be manipulated to enhance absorbency (e.g., channels or grooves may be created to ultimately disperse liquid waste received in the deep containment).

Optional Layers

The disposable absorbent article according to the invention may contain additional layers including an acquisition layer or surge layer, preferably situated between the topsheet and the core. One function of such an acquisition layer is to spread out or disperse liquid flow so that liquid is distributed more evenly over the core surface. This serves to slow down the flow so that the liquid has adequate time to be absorbed by the core. The acquisition layer also serves to prevent the core from being saturated locally, while a substantial remainder of the core is not absorbing any liquid.

Tape Tabs

The article must be secured to the wearer. This is most important with respect to diapers since they are not pulled upon the wearer, like training pants, or incontinent briefs, but are fastened around the wearer. The securing elements compliment the elastic members by effecting a quasi-seal between the wearer and the waist band and leg cuffs, so that liquid is contained within the article which is then absorbed; in other words, so that it does not leak through gaps between the wearer and the edge of the article. The securing elements may be adhesive, mechanical fasteners hook and loop features, or conceivably strings, i.e., anything that will secure one end of the article to the longitudinally opposite end.

In the adhesive devices shown in FIGS. 1, 2 and 4 above, the article 10 is affixed to the wearer by tape fasteners 26 permanently affixed to (e.g., sewn directly into) the backsheet 40. The tape fasteners 26 are contacted with the transversely opposite ear 22 extending from the backsheet where they remain affixed due to an adhesive compound applied to the fasteners 26.

The present inventive design of a disposable absorbent article is well adapted to carry out the diaper or other objects and attain the ends and advantages previously mentioned, as well as others in that area. While description of a particular disposable diaper has been given for the purpose of disclosure, numerous changes in the details of construction of the diaper or other disposable absorbent article, in the arrangement of its part and in the steps of the process of manufacturing the article may be made. These changes will readily suggest themselves to those skilled in the art and are encompassed within the spirit of the invention and the scope of the appended claims.

What is claimed is:

1. A disposable absorbent article having a pair of longitudinally extending side edges and a pair of end edges extending between said side edges, said article comprising:
   a topsheet layer;
   a backsheet layer;
   an absorbent core disposed between said topsheet and said backsheet; and
   a pair of end strips, each end strip being fixed, along a longitudinal direction, at a position intermediate said core and one of said end edges and extending between said side edges, said end strip including at least three sections, each said section having an elasticity from said other sections and a position different from said other sections, including
   a first section having generally elastic properties and laterally extending in generally parallel relation with said end edges,
   a second section disposed immediately subjacent said first section and extending in generally parallel relation with said first section and with said end edges, said second section being characterized in that said first section is substantially more elastic than said second section, and
   a third section positioned immediately subjacent said second section, said third section having an inward portion spaced away from said topsheet and said absorbent core.

2. The disposable absorbent article of claim 1, wherein said second section is formed from an elastic material, said second section having at least one void provided therein, said void being adapted to substantially de-elasticize an area of said second section adjacent said void.

3. The disposable absorbent article of claim 1, wherein each of said first and second sections is secured to said topsheet.

4. The disposable absorbent article of claim 1, wherein said end strip is formed from an elastic material.

5. The disposable absorbent article of claim 4, wherein said second section includes a plurality of voids adapted to substantially de-elasticize said second section.

6. The disposable article of claim 4, wherein said said section section is substantially de-elasticized.

7. The disposable absorbent article of claim 1, wherein said first section forms a waistband portion.

8. The disposable absorbent article of claim 1, wherein said first section is fixed along one of said end edges.

9. The diposable absorbant article of claim 1, wherein said article has a front waist region, a back waist region longitudinally spaced from said front waist region, and a crotch region located between said front waist region and said back waist region, said core being disposed generally in said crotch region, said article further comprising an ear region extending laterally on each side of each of said front waist region and said back waist region, said end strip extending substantially laterally into two of said ear regions.

10. The disposable absorbent article of claim 1, wherein said end strip is formed from an elastic material, and
   wherein said second section is substantially de-elasticized.

11. A disposable absorbent article having a pair of longitudinally extending side edges and a pair of end edges extending between said side edges, said article comprising;
   a top sheet layer;
   a backsheet layer;
   an absorbent core disposed between said topsheet and said backsheet;
   a pair of end strips, each said end strip being fixed, along a longitudinal direction, at a position intermediate said core and one of said end edges and extending between said side edges, said end strip including at least three sections, each said section having an elasticity different from said other sections and a position different from said other sections,
   a first section having generally elastic properties and laterally extending in generally parallel relation with said edges, including a second section immediately subjacent said first section and extending in generally parallel relation therewith, said second section being characterized in that said first section is substantially more elastic than said second section, and a third section positioned immediately subjacent said second section, said third section having an inward portion spaced away from said topsheet and said absorbant core; and wherein said first section, said second section, and said third section form the entirety of said end strip.

12. A disposable absorbent article having a pair of longitudinally extending side edges and a pair of end edges defining a front waist region, a back waist region, and a crotch region, said article comprising:

a top sheet layer;

a backsheet layer;

an absorbent core disposed between said top sheet and said backsheet;

an end strip secured to each one of said front and back waist regions, said end strip having a plurality of sections, each said having generally elastic properties and being positioned differently from said other sections, including, a fixed waist section fixed along a longitudinal direction, at a position intermediate said core and one of said end edges and laterally extending in generally parallel relation with said end edges, said waist section including an elastic end section disposed adjacent said end edge, and an elastic inward section disposed longitudinally inward of said fixed waist section and laterally extending in generally parallel relation therewith, said elastic inward section having a central portion spaced upwardly from said top sheet and said absorbent core; and wherein said fixed waist section further includes an intermediate section disposed between said elastic end section and said elastic inward section, said intermediate section having a plurality of voids provided therein adapted to substantially de-elasticize said intermediate section.

13. The disposable absorbent article of claim 12, wherein said elastic inward section is disposed substantially subjacent said fixed waist section.

14. The disposable absorbent article of claim 12, wherein said intermediate section is disposed substantially subjacent said fixed waist section.

15. The disposable absorbent article of claim 12, wherein said end strip is formed from an elastic material.

16. The disposable absorbent article of claim 12, wherein said waist 88 section includes an elastic end section disposed substantially adjacent said end edge to form an elastic waistband on each of said front and back waist regions.

17. The disposable absorbent article of claim 12, wherein said fixed waist section and said elastic inward section form the entirety of said end strip.

* * * * *